United States Patent [19]
Wiley

[11] 4,311,843
[45] Jan. 19, 1982

[54] DI-N-ALKYL DICARBOXYPYRAZINEDICARBOXYLATES AND FERROUS COMPLEXES

[76] Inventor: Richard H. Wiley, 8 Roosevelt Circle, Palo Alto, Calif. 94306

[21] Appl. No.: 236,154

[22] Filed: Feb. 20, 1981

[51] Int. Cl.$^3$ ............................................. C07D 241/14
[52] U.S. Cl. ...................................... 544/225; 23/932; 252/542; 544/406; 544/408
[58] Field of Search ........................ 544/406, 408, 225

[56] References Cited

U.S. PATENT DOCUMENTS 3,915,974 10/1975 Cairncress ............................ 260/250
4,252,949 2/1981 Wiley ................................... 544/406

FOREIGN PATENT DOCUMENTS 2412110 10/1974 Fed. Rep. of Germany.
348408 10/1960 Switzerland ........................ 544/406

OTHER PUBLICATIONS

Bouyte, et al., *Chem. Abstracts*, 82, No. 4305u.
Bhima, et al., *Chem Abstracts* 70 No. 115129.
Wagner, Romeo, and Zook, Harry, *Synthetic Organic Chemistry*, John Wiley, New York, (1953) p. 4821483.
Walton, et al., *Chem. Abstracts* 75, No. 58158.

*Primary Examiner*—Donald G. Daus
*Assistant Examiner*—Glenna Hendricks

[57] ABSTRACT

Long chain di-n-alkyl esters of dicarboxypyrazinedicarboxylate from n-hexanol, n-octanol, n-decanol, n-dodecanol, and hexadecanol are prepared and characterized as liquid crystals, metals chelates, and surface active agents.

6 Claims, No Drawings

DI-N-ALKYL DICARBOXYPYRAZINEDICARBOXYLATES AND FERROUS COMPLEXES

BACKGROUND

Tetra alkyl esters of pyrazinetetracarboxylic acid (Beilstein Vol. E II 25, p. 187; German Offent No. 2,412,110) and mono esters (U.S. 4,252,949) are well known compounds. The diesters are not. Only one such compound is known—the dimethyl ester (U.S. Pat. No. 3,915,974)—and it is of no interest as a surface active chelating agent or as liquid crystals because of its inherent structure. The dianhydride of pyrazinetetracarboxylic acid, a useful starting material for the preparation of the diesters, is also known (J. Polymer Sci. 7,15, 1969; 9, 1117 1971) as is its reaction with diamines. There is, however, no report of the use of the dianhydride to prepare long chain diesters.

DESCRIPTION OF THE INVENTION

Pyrazinetetracarboxylic anhydride is reacted with controlled amounts of long chain alcohols to give long chain diesters of pyrazine tetracarboxylic acid useful (as such or as their salts) as surface active agents (emulsifiers, antiseptics, detergents); as liquid crystals; and as highly colored ferrous chelates—with moderately strong ($pK_a$ ca. 3.5) acidic functional groups. The anhydride is prepared by previously described techniques. The alcohols are commercially available. The anhydride can be used in its chemically pure condition, or since it is laborious to remove the last traces of metal ions (usually potassium) from the tetra acid used in preparation of the anhydride, it can advantageously be used in a commercially pure form. The resulting diesters are readily separated from such ether insoluble metal salt contaminates by virtue of the ether solubility of the diesters. The surface active properties of the diesters are uniquely combined with their chelating properties. The ferrous ion gives an extremely intense blue-purple colored solution in aqueous media which is detectable at microgram levels, and since the color is immediately discharged by oxidizing agents, is useful as an indicator in redox analyses.

It is assumed that the products of this invention are mixtures of the 2,5- and 2,6- diesters of the 3,6- and 3,5- diacids respectively, with the former predominating. The ratio of the two is demonstrable by nitrogen-15 nuclear magnetic resonance spectroscopy and the two are separable by partition chromatography. For practical purposes the mixture has certain advantages over the purified isomers—such as the lowered melting point of the liquid crystals.

Details of the preparation and properties of the long chain di-n-alkyl esters of pyrazinetetracarboxylic acid are given in the following examples.

EXAMPLE 1

The following procedures are used in the preparation of the anhydride and the diesters. Pyrazinetetracarboxylic acid is purified by recrystallization of its dipotassium; monopotassium; and free acid forms from 2 N and 6 N hydrochloric acid and by ion exchange partition chromatography. The purified acid is heated at 45°–65° C. for 0.5–10 hours with excess acetic anhydride (b.p. 137°–9° C.) using 1 g. of acid in 5 to 50 ml of acetic anhydride. The acetic acid and anhydride are removed under vacuum and the residual solid pyrazinetetracarboxylic anhydride dried at 65° and 0.1 mm vacuum. Further purification is possible, but is not necessary for purposes of preparing the diesters, by vacuum sublimation or by recrystallization (with Norit A) from acetic anhydride or preferably from acetonitrile (dried over Molecular Sieve 4 A.

The pyrazinecarboxylic anhydride thus prepared is reacted with approximately two moles of long chain alcohol per mole of anhydride at 45°–65° C. for 0.5–4 hours. The reaction mixture is taken up in ether or acetonitrile, is filtered to remove traces of insoluble salt and unreacted acid if present, treated with charcoal (Norit A) to remove color if excessive, and evaporated. The residual solid is collected, washed by trituration repeatedly with hexane or ligroin, and recrystallized from ethyl acetate/hexane to remove traces of unreacted alcohol if present and to obtain the pure diester.

EXAMPLE 2

Di-n-hexyl dicarboxypyrazinedicarboxylate. The anhydride obtained from 0.6 g. of the acid in 20 ml of acetic anhydride (at 45° C.) is reacted with 1 ml of n-hexanol (at 45° C.) as described in Example 1. The crude diester product is dissolved in ether and the solution evaporated after filtration leaving the diester which is further purified by washing with ligroin. M.p. 135°–7° C. An alkaline solution of the diester readily disperses carbon black. Anal. Calcd. for $C_{20}H_{28}N_2O_8$: C, 56.60; H, 6.6; N, 6.6. Found: C, 56.54; H, 6.71; N, 6.54. The diester is soluble in alcohol and 0.1 N sodium hydroxide.

EXAMPLE 3

Di-n-octyl dicarboxypyrazinedicarboxylate. To the anhydride prepared as in Example 2 there is added 0.7 ml of n-octyl alcohol. The reaction mixture is held at 45° C. for 30 minutes, evaporated to remove volatile-reactants, and taken up in ether. The ether solution is filtered and evaporated and the residue washed with ligroin to obtain the pure diester product. M.p. 135°–47° C. A blue chelate is formed with copper II Anal. Calcd. for $C_{24}H_{36}N_2O_8$: C, 60.00; H, 7.50; N, 5.83; Neutr. Equiv. 240. Found: C, 60.03; H, 7.42; N, 5.91; Neutr. Equiv. 240, 241.

EXAMPLE 4

Di-n-decyl dicarboxypyrazinedicarboxylate. The anhydride from 1 g of purified acid and 50 ml of acetic anhydride and 1.72 ml of n-decanol are heated at 65° C. for 4 hours. The reaction mixture is taken up in ether and filtered and the ether evaporated leaving the crude diester which is purified by washing with hexane and recrystallization from ethyl acetate/hexane to give the pure product. M.p. 133–150 as liquid crystals. In alcohol-water solution the diester gives a deep blue-purple precipitate of the iron II chelate. The sodium salt slowly precipitates from water. Anal. Calcd. for $C_{28}H_{46}N_2O_8$: Neutr. equiv., 269. Found: Neutr. equiv., 268.

EXAMPLE 5

Di-n-dodecyl dicarboxypyrazinedicarboxylate: The anhydride prepared as in Example 2 from 0.6 g of the tetra acid is reacted with 0.93 ml of dodecyl alcohol. The crude diester is isolated and purified as described in Example 2. The solid product gives a striated solution of liquid crystals in hot ligroin and melts over the range of 120°–135° C. as liquid crystals. The yield of purified diester is 0.8 g. Anal. Calcd. for $C_{32}H_{52}N_4O_8$: Neutr. equiv., 296. Found: Neutr. equiv., 297.

EXAMPLE 6

The di-n-hexadecyl ester is prepared and purified by the procedure given for Example 2. The melting range is 125°–145° C. as liquid crystals.

I claim:

1. A di-n-alkyl dicarboxypyrazinedicarboxylate in which the alkyl groups have six to sixteen carbon atoms.
2. Di-n-hexyl dicarboxypyrazinedicarboxylate.
3. Di-n-octyl dicarboxypyrazinedicarboxylate.
4. Di-n-decyl dicarboxypyrazinedicarboxylate.
5. Di-n-dodecyl dicarboxypyrazinedicarboxylate.
6. Deep blue-purple ferrous didodecyl dicarboxypyrazinedicarboxylate.